(12) United States Patent
Hossainy et al.

(10) Patent No.: US 7,648,727 B2
(45) Date of Patent: Jan. 19, 2010

(54) METHODS FOR MANUFACTURING A COATED STENT-BALLOON ASSEMBLY

(75) Inventors: Syed F. A. Hossainy, Fremont, CA (US); Srinivasan Sridharan, Morgan Hill, CA (US); James Jacobs, Mountain View, CA (US)

(73) Assignee: Advanced Cardiovascular Systems, Inc., Santa Clara, CA (US)

(*) Notice: Subject to any disclaimer, the term of this patent is extended or adjusted under 35 U.S.C. 154(b) by 923 days.

(21) Appl. No.: 10/928,587

(22) Filed: Aug. 26, 2004

(65) Prior Publication Data

US 2006/0043650 A1 Mar. 2, 2006

(51) Int. Cl.
*A61L 33/00* (2006.01)

(52) U.S. Cl. .............. 427/2.25; 427/2.1; 427/2.24; 427/256; 427/271; 623/1.11; 623/1.12; 623/1.42; 623/1.43; 623/1.44; 623/1.46; 604/915; 604/919; 606/108; 606/908

(58) Field of Classification Search ............ 427/2.25; 623/1.11, 1.12, 1.42, 1.43, 1.44, 1.46; 604/915, 604/919; 606/108, 908
See application file for complete search history.

(56) References Cited

U.S. PATENT DOCUMENTS

| | | | |
|---|---|---|---|
| 2,072,303 A | 3/1937 | Herrmann et al. |
| 2,386,454 A | 10/1945 | Frosch et al. |
| 2,701,559 A | 2/1955 | Cooper |
| 3,773,737 A | 11/1973 | Goodman et al. |
| 3,849,514 A | 11/1974 | Gray, Jr. et al. |
| 4,226,243 A | 10/1980 | Shalaby et al. |
| 4,323,071 A | 4/1982 | Simpson et al. |
| 4,329,383 A | 5/1982 | Joh |
| 4,338,942 A | 7/1982 | Fogarty |
| 4,343,931 A | 8/1982 | Barrows |
| 4,439,185 A | 3/1984 | Lundquist |

(Continued)

FOREIGN PATENT DOCUMENTS

DE 42 24 401 1/1994

(Continued)

OTHER PUBLICATIONS

International Search Report for PCT/US2005/030759, filed Aug. 25, 2005, mailed Jun. 26, 2006, 12 pgs.

(Continued)

*Primary Examiner*—Michael Barr
*Assistant Examiner*—Robert S Walters, Jr.
(74) *Attorney, Agent, or Firm*—Squire, Sanders & Dempsey L.L.P.

(57) ABSTRACT

Methods of coating a stent subsequent to mounting or crimping of the stent on a balloon of a catheter assembly are disclosed. One method includes forming a sacrificial layer on a balloon of a catheter assembly; followed by mounting a stent on the balloon, the stent including struts separated by gaps; followed by forming a stent coating on the stent; and followed by removal of the sacrificial layer. Another method includes mounting a stent on a balloon, the stent including struts separated by gaps; followed by forming a sacrificial layer on the balloon in the areas of the gaps between struts of the stent; followed by forming a coating on the stent; and followed by removing the sacrificial layer, wherein the coating remains on an outer surface of the stent.

19 Claims, 3 Drawing Sheets

U.S. PATENT DOCUMENTS

| | | | |
|---|---|---|---|
| 4,489,670 A | 12/1984 | Mosser et al. |
| 4,516,972 A | 5/1985 | Samson et al. |
| 4,529,792 A | 7/1985 | Barrows |
| 4,538,622 A | 9/1985 | Samson et al. |
| 4,554,929 A | 11/1985 | Samson et al. |
| 4,573,470 A | 3/1986 | Samson et al. |
| 4,608,984 A | 9/1986 | Fogarty |
| 4,611,051 A | 9/1986 | Hayes et al. |
| 4,616,593 A | 10/1986 | Kawamura et al. |
| 4,616,652 A | 10/1986 | Simpson |
| 4,629,563 A | 12/1986 | Wrasidlo |
| 4,638,805 A | 1/1987 | Powell |
| 4,656,242 A | 4/1987 | Swan et al. |
| 4,702,252 A | 10/1987 | Brooks et al. |
| 4,733,665 A | 3/1988 | Palmaz |
| 4,748,982 A | 6/1988 | Horzewski et al. |
| 4,774,039 A | 9/1988 | Wrasidlo |
| 4,800,882 A | 1/1989 | Gianturco |
| 4,871,542 A | 10/1989 | Vilhardt |
| 4,880,683 A | 11/1989 | Stow |
| 4,882,168 A | 11/1989 | Casey et al. |
| 4,886,062 A | 12/1989 | Wiktor |
| 4,931,287 A | 6/1990 | Bae et al. |
| 4,941,870 A | 7/1990 | Okada et al. |
| 4,950,227 A | 8/1990 | Savin et al. |
| 4,977,901 A | 12/1990 | Ofstead |
| 4,994,033 A | 2/1991 | Shockey et al. |
| 5,019,096 A | 5/1991 | Fox, Jr. et al. |
| 5,037,392 A | 8/1991 | Hillstead |
| 5,049,132 A | 9/1991 | Shaffer et al. |
| 5,059,169 A | 10/1991 | Zilber |
| 5,064,435 A | 11/1991 | Porter |
| 5,078,720 A | 1/1992 | Burton et al. |
| 5,081,394 A | 1/1992 | Morishita et al. |
| 5,087,244 A | 2/1992 | Wolinsky et al. |
| 5,087,394 A | 2/1992 | Keith |
| 5,100,429 A | 3/1992 | Sinofsky et al. |
| 5,100,992 A | 3/1992 | Cohn et al. |
| 5,102,402 A | 4/1992 | Dror et al. |
| 5,108,416 A | 4/1992 | Ryan et al. |
| 5,112,457 A | 5/1992 | Marchant |
| 5,116,318 A | 5/1992 | Hillstead |
| 5,133,742 A | 7/1992 | Pinchuk |
| 5,147,370 A | 9/1992 | McNamara et al. |
| 5,156,911 A | 10/1992 | Stewart |
| 5,158,548 A | 10/1992 | Lau et al. |
| 5,163,952 A | 11/1992 | Froix |
| 5,165,919 A | 11/1992 | Sasaki et al. |
| 5,171,445 A | 12/1992 | Zepf |
| 5,176,638 A | 1/1993 | Don Michael |
| 5,188,734 A | 2/1993 | Zepf |
| 5,205,822 A | 4/1993 | Johnson et al. |
| 5,213,576 A | 5/1993 | Abiuso et al. |
| 5,219,980 A | 6/1993 | Swidler |
| 5,226,889 A | 7/1993 | Sheiban |
| 5,229,045 A | 7/1993 | Soldani |
| 5,242,399 A | 9/1993 | Lau et al. |
| 5,254,089 A | 10/1993 | Wang |
| 5,254,091 A | 10/1993 | Aliahmad et al. |
| 5,258,020 A | 11/1993 | Froix |
| 5,272,012 A | 12/1993 | Opolski |
| 5,286,254 A | 2/1994 | Shapland et al. |
| 5,292,516 A | 3/1994 | Viegas et al. |
| 5,298,260 A | 3/1994 | Viegas et al. |
| 5,300,295 A | 4/1994 | Viegas et al. |
| 5,306,250 A | 4/1994 | March et al. |
| 5,306,501 A | 4/1994 | Viegas et al. |
| 5,306,786 A | 4/1994 | Moens et al. |
| 5,318,531 A | 6/1994 | Leone |
| 5,328,471 A | 7/1994 | Slepian |
| 5,330,768 A | 7/1994 | Park et al. |
| 5,342,621 A | 8/1994 | Eury |
| 5,344,426 A | 9/1994 | Lau et al. |
| 5,360,401 A | 11/1994 | Turnland et al. |
| 5,380,299 A | 1/1995 | Fearnot et al. |
| 5,387,450 A | 2/1995 | Stewart |
| 5,405,472 A | 4/1995 | Leone |
| 5,409,495 A | 4/1995 | Osborn |
| 5,411,477 A | 5/1995 | Saab |
| 5,412,035 A | 5/1995 | Schmitt et al. |
| 5,417,981 A | 5/1995 | Endo et al. |
| 5,443,496 A | 8/1995 | Schwartz et al. |
| 5,445,646 A | 8/1995 | Euteneuer et al. |
| 5,447,724 A | 9/1995 | Helmus et al. |
| 5,451,233 A | 9/1995 | Yock |
| 5,455,040 A | 10/1995 | Marchant |
| 5,456,661 A | 10/1995 | Narcisco, Jr. |
| 5,456,713 A | 10/1995 | Chuter |
| 5,458,615 A | 10/1995 | Klemm et al. |
| 5,460,610 A | 10/1995 | Don Michael |
| 5,462,990 A | 10/1995 | Hubbell et al. |
| 5,464,650 A | 11/1995 | Berg et al. |
| 5,476,476 A | 12/1995 | Hillstead |
| 5,485,496 A | 1/1996 | Lee et al. |
| 5,496,346 A | 3/1996 | Horzewski et al. |
| 5,501,227 A | 3/1996 | Yock |
| 5,507,768 A | 4/1996 | Lau et al. |
| 5,514,154 A | 5/1996 | Lau et al. |
| 5,516,881 A | 5/1996 | Lee et al. |
| 5,538,493 A | 7/1996 | Gerken et al. |
| 5,545,209 A | 8/1996 | Roberts et al. |
| 5,558,642 A | 9/1996 | Schweich, Jr. et al. |
| 5,569,463 A | 10/1996 | Helmus et al. |
| 5,571,135 A | 11/1996 | Fraser et al. |
| 5,571,567 A | 11/1996 | Shah |
| 5,578,073 A | 11/1996 | Haimovich et al. |
| 5,584,877 A | 12/1996 | Miyake et al. |
| 5,595,722 A | 1/1997 | Grainger et al. |
| 5,599,307 A | 2/1997 | Bacher et al. |
| 5,605,696 A | 2/1997 | Eury et al. |
| 5,607,467 A | 3/1997 | Froix |
| 5,609,629 A | 3/1997 | Fearnot et al. |
| 5,610,241 A | 3/1997 | Lee et al. |
| 5,611,775 A | 3/1997 | Machold et al. |
| 5,616,338 A | 4/1997 | Fox, Jr. et al. |
| 5,620,420 A | 4/1997 | Kriesel |
| 5,624,411 A | 4/1997 | Tuch |
| 5,628,730 A | 5/1997 | Shapland et al. |
| 5,637,113 A | 6/1997 | Tartaglia et al. |
| 5,644,020 A | 7/1997 | Timmermann et al. |
| 5,645,559 A | 7/1997 | Hachtman et al. |
| 5,649,977 A | 7/1997 | Campbell |
| 5,653,691 A | 8/1997 | Rupp et al. |
| 5,656,082 A | 8/1997 | Takatsuki et al. |
| 5,658,995 A | 8/1997 | Kohn et al. |
| 5,667,523 A | 9/1997 | Bynon et al. |
| 5,667,767 A | 9/1997 | Greff et al. |
| 5,670,558 A | 9/1997 | Onishi et al. |
| 5,674,242 A | 10/1997 | Phan et al. |
| 5,679,400 A | 10/1997 | Tuch |
| 5,695,498 A | 12/1997 | Tower |
| 5,700,286 A | 12/1997 | Tartaglia et al. |
| 5,702,754 A | 12/1997 | Zhong |
| 5,707,385 A | 1/1998 | Williams |
| 5,711,958 A | 1/1998 | Cohn et al. |
| 5,716,981 A | 2/1998 | Hunter et al. |
| 5,720,726 A | 2/1998 | Marcadis et al. |
| 5,721,131 A | 2/1998 | Rudolph et al. |
| 5,723,219 A | 3/1998 | Kolluri et al. |
| 5,728,068 A | 3/1998 | Leone et al. |
| 5,733,327 A | 3/1998 | Igaki et al. |
| 5,735,897 A | 4/1998 | Buirge |
| 5,746,745 A | 5/1998 | Abele et al. |
| 5,746,998 A | 5/1998 | Torchilin et al. |

| | | | | | |
|---|---|---|---|---|---|
| 5,759,205 A | 6/1998 | Valentini | 6,056,993 A | 5/2000 | Leidner et al. |
| 5,759,474 A | 6/1998 | Rupp et al. | 6,059,810 A | 5/2000 | Brown et al. |
| 5,770,609 A | 6/1998 | Grainger et al. | 6,060,451 A | 5/2000 | DiMaio et al. |
| 5,776,184 A | 7/1998 | Tuch | 6,060,518 A | 5/2000 | Kabanov et al. |
| 5,783,657 A | 7/1998 | Pavlin et al. | 6,063,092 A | 5/2000 | Shin |
| 5,788,979 A | 8/1998 | Alt et al. | 6,066,156 A | 5/2000 | Yan |
| 5,800,392 A | 9/1998 | Racchini | 6,080,488 A | 6/2000 | Hostettler et al. |
| 5,807,244 A | 9/1998 | Barot | 6,086,610 A | 7/2000 | Duerig et al. |
| 5,810,871 A | 9/1998 | Tuckey et al. | 6,086,773 A | 7/2000 | Dufresne et al. |
| 5,820,917 A | 10/1998 | Tuch | 6,090,330 A | 7/2000 | Gawa et al. |
| 5,823,996 A | 10/1998 | Sparks | 6,096,070 A | 8/2000 | Ragheb et al. |
| 5,824,048 A | 10/1998 | Tuch | 6,099,559 A | 8/2000 | Nolting |
| 5,824,049 A | 10/1998 | Ragheb et al. | 6,099,562 A | 8/2000 | Ding et al. |
| 5,830,178 A | 11/1998 | Jones et al. | 6,106,530 A | 8/2000 | Harada |
| 5,830,179 A | 11/1998 | Mikus et al. | 6,106,889 A * | 8/2000 | Beavers et al. ................ 427/2.1 |
| 5,830,217 A | 11/1998 | Ryan | 6,110,180 A | 8/2000 | Foreman et al. |
| 5,833,644 A | 11/1998 | Zadno-Azizi et al. | 6,110,188 A | 8/2000 | Narciso, Jr. |
| 5,833,659 A | 11/1998 | Kranys | 6,110,483 A | 8/2000 | Whitbourne et al. |
| 5,836,965 A | 11/1998 | Jendersee et al. | 6,113,629 A | 9/2000 | Ken |
| 5,837,008 A | 11/1998 | Berg et al. | 6,120,477 A | 9/2000 | Campbell et al. |
| 5,837,313 A | 11/1998 | Ding et al. | 6,120,491 A | 9/2000 | Kohn et al. |
| 5,843,033 A | 12/1998 | Ropiak | 6,120,536 A | 9/2000 | Ding et al. |
| 5,843,119 A | 12/1998 | Shmulewitz | 6,120,788 A | 9/2000 | Barrows |
| 5,843,172 A | 12/1998 | Yan | 6,120,904 A | 9/2000 | Hostettler et al. |
| 5,846,247 A | 12/1998 | Unsworth et al. | 6,121,027 A | 9/2000 | Clapper et al. |
| 5,849,859 A | 12/1998 | Acemoglu | 6,123,712 A | 9/2000 | Di Caprio et al. |
| 5,851,508 A | 12/1998 | Greff et al. | 6,129,761 A | 10/2000 | Hubbell |
| 5,854,376 A | 12/1998 | Higashi | 6,136,333 A | 10/2000 | Cohn et al. |
| 5,855,598 A | 1/1999 | Pinchuk | 6,140,127 A | 10/2000 | Sprague |
| 5,857,998 A | 1/1999 | Barry | 6,143,354 A | 11/2000 | Koulik et al. |
| 5,858,746 A | 1/1999 | Hubbell et al. | 6,153,252 A | 11/2000 | Hossainy et al. |
| 5,860,954 A | 1/1999 | Ropiak | 6,159,227 A | 12/2000 | Di Caprio et al. |
| 5,865,814 A | 2/1999 | Tuch | 6,159,229 A | 12/2000 | Jendersee et al. |
| 5,869,127 A | 2/1999 | Zhong | 6,159,978 A | 12/2000 | Myers et al. |
| 5,873,904 A | 2/1999 | Ragheb et al. | 6,165,212 A | 12/2000 | Dereume et al. |
| 5,876,426 A | 3/1999 | Kume et al. | 6,168,617 B1 | 1/2001 | Blaeser et al. |
| 5,876,433 A | 3/1999 | Lunn | 6,172,167 B1 | 1/2001 | Stapert et al. |
| 5,877,224 A | 3/1999 | Brocchini et al. | 6,174,316 B1 | 1/2001 | Tuckey et al. |
| 5,879,713 A | 3/1999 | Roth et al. | 6,177,523 B1 | 1/2001 | Reich et al. |
| 5,893,852 A | 4/1999 | Morales | 6,180,632 B1 | 1/2001 | Myers et al. |
| 5,897,911 A | 4/1999 | Loeffler | 6,193,727 B1 | 2/2001 | Foreman et al. |
| 5,902,875 A | 5/1999 | Roby et al. | 6,203,551 B1 | 3/2001 | Wu |
| 5,905,168 A | 5/1999 | Dos Santos et al. | 6,211,249 B1 | 4/2001 | Cohn et al. |
| 5,910,564 A | 6/1999 | Gruning et al. | 6,214,901 B1 | 4/2001 | Chudzik et al. |
| 5,914,387 A | 6/1999 | Roby et al. | 6,217,586 B1 | 4/2001 | Mackenzie |
| 5,919,893 A | 7/1999 | Roby et al. | 6,231,600 B1 | 5/2001 | Zhong |
| 5,921,416 A | 7/1999 | Uehara | 6,240,616 B1 | 6/2001 | Yan |
| 5,925,720 A | 7/1999 | Kataoka et al. | 6,245,076 B1 | 6/2001 | Yan |
| 5,932,299 A | 8/1999 | Katoot | 6,245,753 B1 | 6/2001 | Byun et al. |
| 5,948,018 A | 9/1999 | Dereume et al. | 6,245,760 B1 | 6/2001 | He et al. |
| 5,955,509 A | 9/1999 | Webber et al. | 6,248,129 B1 | 6/2001 | Froix |
| 5,958,385 A | 9/1999 | Tondeur et al. | 6,251,136 B1 | 6/2001 | Guruwaiya et al. |
| 5,962,138 A | 10/1999 | Kolluri et al. | 6,254,632 B1 | 7/2001 | Wu et al. |
| 5,968,091 A | 10/1999 | Pinchuk et al. | 6,258,099 B1 | 7/2001 | Mareiro et al. |
| 5,971,954 A | 10/1999 | Conway et al. | 6,258,121 B1 | 7/2001 | Yang et al. |
| 5,976,155 A | 11/1999 | Foreman et al. | 6,258,371 B1 | 7/2001 | Koulik et al. |
| 5,980,928 A | 11/1999 | Terry | 6,262,034 B1 | 7/2001 | Mathiowitz et al. |
| 5,980,972 A | 11/1999 | Ding | 6,270,788 B1 | 8/2001 | Koulik et al. |
| 5,997,517 A | 12/1999 | Whitbourne | 6,277,110 B1 | 8/2001 | Morales |
| 6,010,530 A | 1/2000 | Goicoechea | 6,277,449 B1 | 8/2001 | Kolluri et al. |
| 6,011,125 A | 1/2000 | Lohmeijer et al. | 6,283,947 B1 | 9/2001 | Mirzaee |
| 6,013,099 A | 1/2000 | Dinh et al. | 6,283,949 B1 | 9/2001 | Roorda |
| 6,015,541 A | 1/2000 | Greff et al. | 6,284,305 B1 | 9/2001 | Ding et al. |
| 6,027,510 A | 2/2000 | Alt | 6,287,628 B1 | 9/2001 | Hossainy et al. |
| 6,033,582 A | 3/2000 | Lee et al. | 6,299,604 B1 | 10/2001 | Ragheb et al. |
| 6,034,204 A | 3/2000 | Mohr et al. | 6,306,176 B1 | 10/2001 | Whitbourne |
| 6,042,875 A | 3/2000 | Ding et al. | 6,331,313 B1 | 12/2001 | Wong et al. |
| 6,045,899 A | 4/2000 | Wang et al. | 6,335,029 B1 | 1/2002 | Kamath et al. |
| 6,051,021 A | 4/2000 | Frid | 6,344,035 B1 | 2/2002 | Chudzik et al. |
| 6,051,576 A | 4/2000 | Ashton et al. | 6,346,110 B2 | 2/2002 | Wu |
| 6,051,648 A | 4/2000 | Rhee et al. | 6,358,556 B1 | 3/2002 | Ding et al. |
| 6,054,553 A | 4/2000 | Groth et al. | 6,379,381 B1 | 4/2002 | Hossainy et al. |
| 6,056,906 A | 5/2000 | Werneth et al. | 6,387,379 B1 | 5/2002 | Goldberg et al. |

| | | |
|---|---|---|
| 6,395,325 B1 | 5/2002 | Hedge et al. |
| 6,395,326 B1 | 5/2002 | Castro et al. |
| 6,419,692 B1 | 7/2002 | Yang et al. |
| 6,447,835 B1 | 9/2002 | Wang et al. |
| 6,451,373 B1 | 9/2002 | Hossainy et al. |
| 6,454,738 B1 | 9/2002 | Tran et al. |
| 6,458,138 B1 * | 10/2002 | Sydney et al. ............... 606/108 |
| 6,482,834 B2 | 11/2002 | Spada et al. |
| 6,494,862 B1 | 12/2002 | Ray et al. |
| 6,503,538 B1 | 1/2003 | Chu et al. |
| 6,503,556 B2 | 1/2003 | Harish et al. |
| 6,503,954 B1 | 1/2003 | Bhat et al. |
| 6,506,437 B1 | 1/2003 | Harish et al. |
| 6,517,889 B1 | 2/2003 | Jayaraman |
| 6,524,347 B1 | 2/2003 | Myers et al. |
| 6,527,801 B1 | 3/2003 | Dutta |
| 6,527,863 B1 | 3/2003 | Pacetti et al. |
| 6,528,526 B1 | 3/2003 | Myers et al. |
| 6,530,950 B1 | 3/2003 | Alvarado et al. |
| 6,530,951 B1 | 3/2003 | Bates et al. |
| 6,540,776 B2 | 4/2003 | Sanders Millare et al. |
| 6,544,223 B1 | 4/2003 | Kokish |
| 6,544,543 B1 | 4/2003 | Mandrusov et al. |
| 6,544,582 B1 | 4/2003 | Yoe |
| 6,555,059 B1 | 4/2003 | Myrick et al. |
| 6,555,157 B1 | 4/2003 | Hossainy |
| 6,558,733 B1 | 5/2003 | Hossainy et al. |
| 6,562,136 B1 | 5/2003 | Chappa et al. |
| 6,565,659 B1 | 5/2003 | Pacetti et al. |
| 6,572,644 B1 | 6/2003 | Moein |
| 6,585,755 B2 | 7/2003 | Jackson et al. |
| 6,585,765 B1 | 7/2003 | Hossainy et al. |
| 6,585,926 B1 | 7/2003 | Mirzaee |
| 6,605,154 B1 | 8/2003 | Villareal |
| 6,616,765 B1 | 9/2003 | Hossainy et al. |
| 6,623,448 B2 | 9/2003 | Slater |
| 6,625,486 B2 | 9/2003 | Lundkvist et al. |
| 6,645,135 B1 | 11/2003 | Bhat |
| 6,645,195 B1 | 11/2003 | Bhat et al. |
| 6,656,216 B1 | 12/2003 | Hossainy et al. |
| 6,656,506 B1 | 12/2003 | Wu et al. |
| 6,660,034 B1 | 12/2003 | Mandrusov et al. |
| 6,663,662 B2 | 12/2003 | Pacetti et al. |
| 6,663,880 B1 | 12/2003 | Roorda et al. |
| 6,666,880 B1 | 12/2003 | Chiu et al. |
| 6,673,154 B1 | 1/2004 | Pacetti et al. |
| 6,673,385 B1 | 1/2004 | Ding et al. |
| 6,682,383 B2 * | 1/2004 | Cho et al. ..................... 445/50 |
| 6,689,099 B2 | 2/2004 | Mirzaee |
| 6,695,920 B1 | 2/2004 | Pacetti et al. |
| 6,706,013 B1 | 3/2004 | Bhat et al. |
| 6,709,514 B1 | 3/2004 | Hossainy |
| 6,712,845 B2 | 3/2004 | Hossainy |
| 6,713,119 B2 | 3/2004 | Hossainy et al. |
| 6,716,444 B1 | 4/2004 | Castro et al. |
| 6,723,120 B2 | 4/2004 | Yan |
| 6,733,768 B2 | 5/2004 | Hossainy et al. |
| 6,740,040 B1 | 5/2004 | Mandrusov et al. |
| 6,743,462 B1 | 6/2004 | Pacetti |
| 6,749,626 B1 | 6/2004 | Bhat et al. |
| 6,753,071 B1 | 6/2004 | Pacetti |
| 6,758,859 B1 | 7/2004 | Dang et al. |
| 6,759,054 B2 | 7/2004 | Chen et al. |
| 6,764,505 B1 | 7/2004 | Hossainy et al. |
| 6,861,088 B2 | 3/2005 | Weber et al. |
| 6,865,810 B2 | 3/2005 | Stinson |
| 6,869,443 B2 | 3/2005 | Buscemi et al. |
| 6,878,160 B2 | 4/2005 | Gilligan et al. |
| 6,887,270 B2 | 5/2005 | Miller et al. |
| 6,887,485 B2 | 5/2005 | Fitzhugh et al. |
| 6,890,546 B2 | 5/2005 | Mollison et al. |
| 6,899,731 B2 | 5/2005 | Li et al. |
| 2001/0007083 A1 | 7/2001 | Roorda |
| 2001/0014717 A1 | 8/2001 | Hossainy et al. |
| 2001/0016753 A1 | 8/2001 | Caprio et al. |
| 2001/0018469 A1 | 8/2001 | Chen et al. |
| 2001/0020011 A1 | 9/2001 | Mathiowitz et al. |
| 2001/0029351 A1 | 10/2001 | Falotico et al. |
| 2001/0032013 A1 | 10/2001 | Marton |
| 2001/0037145 A1 | 11/2001 | Guruwaiya et al. |
| 2001/0051608 A1 | 12/2001 | Mathiowitz et al. |
| 2002/0005206 A1 | 1/2002 | Falotico et al. |
| 2002/0007213 A1 | 1/2002 | Falotico et al. |
| 2002/0007214 A1 | 1/2002 | Falotico |
| 2002/0007215 A1 | 1/2002 | Falotico et al. |
| 2002/0009604 A1 | 1/2002 | Zamora et al. |
| 2002/0016625 A1 | 2/2002 | Falotico et al. |
| 2002/0032414 A1 | 3/2002 | Ragheb et al. |
| 2002/0032434 A1 | 3/2002 | Chudzik et al. |
| 2002/0051730 A1 | 5/2002 | Bodnar et al. |
| 2002/0071822 A1 | 6/2002 | Uhrich |
| 2002/0077693 A1 | 6/2002 | Barclay et al. |
| 2002/0082679 A1 | 6/2002 | Sirhan et al. |
| 2002/0087123 A1 | 7/2002 | Hossainy et al. |
| 2002/0091433 A1 | 7/2002 | Ding et al. |
| 2002/0094440 A1 | 7/2002 | Llanos et al. |
| 2002/0111590 A1 | 8/2002 | Davila et al. |
| 2002/0120326 A1 | 8/2002 | Michal |
| 2002/0123801 A1 | 9/2002 | Pacetti et al. |
| 2002/0142039 A1 | 10/2002 | Claude |
| 2002/0155212 A1 | 10/2002 | Hossainy |
| 2002/0165608 A1 | 11/2002 | Llanos et al. |
| 2002/0176849 A1 | 11/2002 | Slepian |
| 2002/0183581 A1 | 12/2002 | Yoe et al. |
| 2002/0188037 A1 | 12/2002 | Chudzik et al. |
| 2002/0188277 A1 | 12/2002 | Roorda et al. |
| 2003/0004141 A1 | 1/2003 | Brown |
| 2003/0028243 A1 | 2/2003 | Bates et al. |
| 2003/0028244 A1 | 2/2003 | Bates et al. |
| 2003/0031780 A1 | 2/2003 | Chudzik et al. |
| 2003/0032767 A1 | 2/2003 | Tada et al. |
| 2003/0036794 A1 | 2/2003 | Ragheb et al. |
| 2003/0039689 A1 | 2/2003 | Chen et al. |
| 2003/0040712 A1 | 2/2003 | Ray et al. |
| 2003/0040790 A1 | 2/2003 | Furst |
| 2003/0055482 A1 | 3/2003 | Schwager et al. |
| 2003/0059520 A1 | 3/2003 | Chen et al. |
| 2003/0060877 A1 | 3/2003 | Falotico et al. |
| 2003/0065377 A1 | 4/2003 | Davila et al. |
| 2003/0072868 A1 | 4/2003 | Harish et al. |
| 2003/0073961 A1 | 4/2003 | Happ |
| 2003/0083646 A1 | 5/2003 | Sirhan et al. |
| 2003/0083739 A1 | 5/2003 | Cafferata |
| 2003/0097088 A1 | 5/2003 | Pacetti |
| 2003/0097173 A1 | 5/2003 | Dutta |
| 2003/0099712 A1 | 5/2003 | Jayaraman |
| 2003/0105518 A1 | 6/2003 | Dutta |
| 2003/0113439 A1 | 6/2003 | Pacetti et al. |
| 2003/0150380 A1 | 8/2003 | Yoe |
| 2003/0157241 A1 | 8/2003 | Hossainy et al. |
| 2003/0158517 A1 | 8/2003 | Kokish |
| 2003/0190406 A1 | 10/2003 | Hossainy et al. |
| 2003/0207020 A1 | 11/2003 | Villareal |
| 2003/0211230 A1 | 11/2003 | Pacetti et al. |
| 2004/0018296 A1 | 1/2004 | Castro et al. |
| 2004/0029952 A1 | 2/2004 | Chen et al. |
| 2004/0047978 A1 | 3/2004 | Hossainy et al. |
| 2004/0047980 A1 | 3/2004 | Pacetti et al. |
| 2004/0052858 A1 | 3/2004 | Wu et al. |
| 2004/0052859 A1 | 3/2004 | Wu et al. |
| 2004/0054104 A1 | 3/2004 | Pacetti |
| 2004/0060508 A1 | 4/2004 | Pacetti et al. |
| 2004/0062853 A1 | 4/2004 | Pacetti et al. |
| 2004/0063805 A1 | 4/2004 | Pacetti et al. |
| 2004/0071861 A1 | 4/2004 | Mandrusov et al. |
| 2004/0072922 A1 | 4/2004 | Hossainy et al. |

| | | | | | | |
|---|---|---|---|---|---|---|
| 2004/0073298 | A1 | 4/2004 | Hossainy | WO | WO 96/40174 | 12/1996 |
| 2004/0086542 | A1 | 5/2004 | Hossainy et al. | WO | WO 97/10011 | 3/1997 |
| 2004/0086550 | A1 | 5/2004 | Roorda et al. | WO | WO 97/45105 | 12/1997 |
| 2004/0096504 | A1 | 5/2004 | Michal | WO | WO 97/46590 | 12/1997 |
| 2004/0098117 | A1 | 5/2004 | Hossainy et al. | WO | WO 98/07390 | 2/1998 |
| 2004/0111144 | A1 | 6/2004 | Lawin et al. | WO | WO 98/08463 | 3/1998 |
| 2004/0148010 | A1 * | 7/2004 | Rush ................... 623/1.13 | WO | WO 98/17331 | 4/1998 |
| 2005/0037052 | A1 | 2/2005 | Udipi et al. | WO | WO 98/32398 | 7/1998 |
| 2005/0038134 | A1 | 2/2005 | Loomis et al. | WO | WO 98/36784 | 8/1998 |
| 2005/0038497 | A1 | 2/2005 | Neuendorf et al. | WO | WO 99/01118 | 1/1999 |
| 2005/0043786 | A1 | 2/2005 | Chu et al. | WO | WO 99/38546 | 8/1999 |
| 2005/0049693 | A1 | 3/2005 | Walker | WO | WO 99/63981 | 12/1999 |
| 2005/0049694 | A1 | 3/2005 | Neary | WO | WO 00/02599 | 1/2000 |
| 2005/0054774 | A1 | 3/2005 | Kangas | WO | WO 00/12147 | 3/2000 |
| 2005/0055044 | A1 | 3/2005 | Kangas | WO | WO 00/18446 | 4/2000 |
| 2005/0055078 | A1 | 3/2005 | Campbell | WO | WO 00/64506 | 11/2000 |
| 2005/0060020 | A1 | 3/2005 | Jenson | WO | WO 01/00109 * | 1/2001 |
| 2005/0064088 | A1 | 3/2005 | Fredrickson | WO | WO 01/01890 | 1/2001 |
| 2005/0065501 | A1 | 3/2005 | Wallace | WO | WO 01/15751 | 3/2001 |
| 2005/0065545 | A1 | 3/2005 | Wallace | WO | WO 01/17459 | 3/2001 |
| 2005/0065593 | A1 | 3/2005 | Chu et al. | WO | WO 01/17577 | 3/2001 |
| 2005/0074406 | A1 | 4/2005 | Couvillon, Jr. et al. | WO | WO 01/45763 | 6/2001 |
| 2005/0074545 | A1 | 4/2005 | Thomas | WO | WO 01/49338 | 7/2001 |
| 2005/0075714 | A1 | 4/2005 | Cheng et al. | WO | WO 01/51027 | 7/2001 |
| 2005/0079274 | A1 | 4/2005 | Palasis et al. | WO | WO 01/52772 | 7/2001 |
| 2005/0084515 | A1 | 4/2005 | Udipi et al. | WO | WO 01/74414 | 10/2001 |
| 2005/0106210 | A1 | 5/2005 | Ding et al. | WO | WO 01/91918 | 12/2001 |
| 2005/0113903 | A1 | 5/2005 | Rosenthal et al. | WO | WO 02/03890 | 1/2002 |
| 2006/0047336 | A1 * | 3/2006 | Gale et al. ................ 623/1.11 | WO | WO 02/26162 | 4/2002 |
| | | | | WO | WO 02/34311 | 5/2002 |
| | | | | WO | WO 02/056790 | 7/2002 |
| | | | | WO | WO 02/058753 | 8/2002 |
| | | | | WO | WO 02/102283 | 12/2002 |
| | | | | WO | WO 03/000308 | 1/2003 |
| | | | | WO | WO 03/022323 | 3/2003 |
| | | | | WO | WO 03/028780 | 4/2003 |
| | | | | WO | WO 03/037223 | 5/2003 |
| | | | | WO | WO 03/039612 | 5/2003 |
| | | | | WO | WO 03/080147 | 10/2003 |
| | | | | WO | WO 03/082368 | 10/2003 |
| | | | | WO | WO 2004/000383 | 12/2003 |
| | | | | WO | WO 2004/009145 | 1/2004 |
| | | | | WO | WO 2005/082578 | 9/2005 |
| | | | | WO | WO 2006/026201 | 3/2006 |

FOREIGN PATENT DOCUMENTS

| | | |
|---|---|---|
| EP | 0 301 856 | 2/1989 |
| EP | 0 396 429 | 11/1990 |
| EP | 0 553 960 | 8/1993 |
| EP | 0 604 022 | 6/1994 |
| EP | 0 623 354 | 11/1994 |
| EP | 0 627 226 | 12/1994 |
| EP | 0 655 023 | 8/1995 |
| EP | 0 701 802 | 3/1996 |
| EP | 0 716 836 | 6/1996 |
| EP | 0 732 087 | 9/1996 |
| EP | 0 809 999 | 12/1997 |
| EP | 0 832 655 | 4/1998 |
| EP | 0 834 293 | 4/1998 |
| EP | 0 850 651 | 7/1998 |
| EP | 0 879 595 | 11/1998 |
| EP | 0 910 584 | 4/1999 |
| EP | 0 923 953 | 6/1999 |
| EP | 0 953 320 | 11/1999 |
| EP | 0 970 711 | 1/2000 |
| EP | 0 974 315 | 1/2000 |
| EP | 0 982 041 | 3/2000 |
| EP | 1 023 879 | 8/2000 |
| EP | 1 034 752 | 9/2000 |
| EP | 1 192 957 | 4/2002 |
| EP | 1 273 314 | 1/2003 |
| FR | 2 753 907 | 4/1998 |
| JP | 2001-190687 | 7/2001 |
| SU | 872531 | 10/1981 |
| SU | 876663 | 10/1981 |
| SU | 905228 | 2/1982 |
| SU | 790725 | 2/1983 |
| SU | 1016314 | 5/1983 |
| SU | 811750 | 9/1983 |
| SU | 1293518 | 2/1987 |
| SU | 1477423 | 5/1989 |
| WO | WO 91/11176 | 8/1991 |
| WO | WO 91/12846 | 9/1991 |
| WO | WO 94/09760 | 5/1994 |
| WO | WO 95/10989 | 4/1995 |
| WO | WO 95/24929 | 9/1995 |
| WO | WO 95/33422 | 12/1995 |

OTHER PUBLICATIONS

U.S. Appl. No. 10/630,250, filed Jul. 30, 2003, Pacetti et al.
U.S. Appl. No. 10/738,704, filed Dec. 16, 2003 Pacetti et al.
U.S. Appl. No. 10/741,214, filed Dec. 19, 2003, Pacetti.
U.S. Appl. No. 10/750,139, filed Dec. 30, 2003, DesNoyer et al.
U.S. Appl. No. 10/805,036, filed Mar. 16, 2004, Pacetti.
U.S. Appl. No. 10/816,072, filed Mar. 31, 2004, Dugan et al.
U.S. Appl. No. 10/835,656, filed Apr. 30, 2004, Hossainy et al.
U.S. Appl. No. 10/855,294, filed May 26, 2004, Pacetti et al.
ACS RX Multi-Link™ *Coronary Stent System Brochure* (Undated), 7 pages.
Anonymous, *Cardiologists Draw—Up The Dream Stent*, Clinica 710:15 (Jun. 17, 1996), http://www.dialogweb.com/cgi/document?reg=1061848202959, printed Aug. 25, 2003 (2 pages).
Anonymous, *Heparin-Coated Stents Cut Complications by 30%*, Clinica 732:17 (Nov. 18, 1996), http://www.dialogweb.com/cgi/document?reg=1061847871753, printed Aug. 25, 2003 (2 pages).
Anonymous, *Rolling Therapeutic Agent Loading Device for Therapeutic Agent Delivery or Coated Stent* (Abstract 434009), Res. Disclos. pp. 974-975 (Jun. 2000).
Anonymous, *Stenting Continues to Dominate Cardiology*, Clinica 720:22 (Sept. 2, 1996), http://www.dialogweb.com/cgi/document?reg=1061848017752, printed Aug. 25, 2003 (2 pages).
Aoyagi et al., *Preparation of Cross-Linked Aliphatic Polyester and Application to Thermo-Responsive Material*, Journal of Controlled Release 32:87-96 (1994).

Barath et al., *Low Dose of Antitumor Agents Prevents Smooth Muscle Cell Proliferation After Endothelial Injury*, JACC 13(2): 252A (Abstract) (Feb. 1989).

Barbucci et al., *Coating of Commercially Available Materials With a New Heparinizable Material*, J. Biomed. Mater. Res. 25:1259-1274 (Oct. 1991).

Chung et al., *Inner Core Segment Design for Drug Delivery Control of Thermo-Responsive Polymeric Micelles*, Journal of Controlled Release 65:93-103 (2000).

Dev et al., *Kinetics of Drug Delivery to the Arterial Wall Via Polyurethane-Coated Removable Nitinol Stent:: Comparative Study of Two Drugs*, Catheterization and Cardiovascular Diagnosis 34:272-278 (1995).

Dichek et al., *Seeding of Intravascular Stents with Genetically Engineered Endothelial Cells*, Circ. 80(5):1347-1353 (Nov. 1989).

Eigler et al., *Local Arterial Wall Drug Delivery from a Polymer Coated Removable Metallic Stent: Kinetics, Distribution, and Bioactivity of Forskolin*, JACC, 4A (701-1), Abstract (Feb. 1994).

Helmus, *Overview of Biomedical Materials*, MRS Bulletin, pp. 33-38 (Sept. 1991).

Herdeg et al., *Antiproliferative Stent Coatings: Taxol and Related Compounds*, Semin. Intervent. Cardiol. 3:197-199 (1998).

Huang et al., *Biodegradable Polymers Derived from Aminoacids*, Macromol. Symp. 144, 7-32 (1999).

Inoue et al., *An AB Block Copolymer of Oligo(Methyl Methacrylate) and Poly(Acrylic Acid) for Micellar Delivery of Hydrophobic Durgs*, Journal of Controlled Release 51:221-229 (1998).

Kataoka et al., *Block Copolymer Micelles as Vehicles for Drug Delivery*, Journal of Controlled Release 24:119-132 (1993).

Katsarava et al., *Amino Acid-Based Bioanalogous Polymers. Synthesis and Study of Regular Poly(esteramides)s Based on Bis(α-amino acid)α,ω-Alkylene Diesters, and Aliphatic Dicarbolic Acids*, Journal of Polymer Science, Part A: Polymer Chemistry, 3(4), 391-407 (1999).

Levy et al., *Strategies For Treating Arterial Restenosis Using Polymeric Controlled Release Implants*, Biotechnol. Bioact. Polym. [Proc. Am. Chem. Soc. Symp.], pp. 259-268 (1994).

Liu et al., *Drug Release Characteristics of Unimolecular Polymeric Micelles*, Journal of Controlled Release 68:167-174 (2000).

Marconi et al., *Covalent Bonding of Heparin to a Vinyl Copolymer for Biomedical Applications*, Biomaterials 18(12):885-890 (1997).

Matsumaru et al., *Embolic Materials For Endovascular Treatment of Cerebral Lesions*, J. Biomater. Sci. Polymer Edn 8(7):555-569 (1997).

Miyazaki et al., *Antitumor Effect of Implanted Ethylene-Vinyl Alcohol Copolymer Matrices Containing Anticancer Agents on Ehrlich Ascites Carcinoma and P388 Leukemia in Mice*, Chem. Pharm. Bull. 33(6)2490-2498 (1985).

Miyazawa et al., *Effects of Pemirolast and Tranilast on Intimal Thickening After Arterial Injury in the Rat*, J. Cardiovasc. Pharmacol., pp. 157-162 (1997).

Nordrehaug et al., *A Novel Biocompatible Coating Applied to Coronary Stents*, EPO Heart Journal 14, p. 321 (P1694), Abstr. Suppl. (1993).

Ohsawa et al., *Preventive Effects of an Antiallergic Drug, Pemirolast Potassium, on Restenosis After Percutaneous Transluminal Coronary Angioplasty*, American Heart Journal 136(6):1081-1087 (Dec. 1998).

Ozaki et al., *New Stent Technologies*, Progress in Cardiovascular Diseases, vol. XXXIX(2):129-140 (Sept./Oct. 1996).

Pechar et al., *Poly(ethylene glycol)Multiblock Copolymer as a Carrier of Anti-Cancer Drug Doxorubicin*, Bioconjucate Chemistry 11(2):131-139 (Mar./Apr. 2000).

Peng et al., *Role of Polymers in Improving the Results of Stenting in Coronary Arteries*, Biomaterials 17:685-694 (1996).

Saotome, et al., *Novel Enzymatically Degradable Polymers Comprising α-Amino Acid, 1,2-Ethanediol, and Adipic Acid*, Chemistry Letters, pp. 21-24, (1991).

Shigeno, *Prevention of Cerebrovascular Spasm by Bosentan, Novel Endothelin Receptor*, Chemical Abstract 125:212307 (1996).

van Beusekom et al., *Coronary Stent Coatings*, Coronary Artery Disease 5(7):590-596 (Jul. 1994).

Wilensky et al., *Methods and Devices for Local Drug Delivery in Coronary and Peripheral Arteries*, Trends Cardiovasc. Med. 3(5):163-170 (1993).

Yokoyama et al., *Characterization of Physical Entrapment and Chemical Conjugation of Adriamycin in Polymeric Micelles and their Design for in Vivo Delivery to aSolid Tumor*, Journal of Controlled Release 50:79-92 (1998).

\* cited by examiner

METHODS FOR MANUFACTURING A COATED STENT-BALLOON ASSEMBLY

BACKGROUND OF THE INVENTION

1. Field of the Invention

The invention relates to methods for coating stents. In particular, the methods are directed to coating a stent mounted on a balloon of a catheter assembly.

2. Description of the Background

Stents are being modified to provide drug delivery capabilities. A polymeric carrier, impregnated with a drug or therapeutic substance is coated on a stent. The conventional method of coating is by, for example, applying a composition including a solvent, a polymer dissolved in the solvent, and a therapeutic substance dispersed in the blend to the stent by immersing the stent in the composition or by spraying the composition onto the stent. The solvent is allowed to evaporate, leaving on the stent strut surfaces a coating of the polymer and the therapeutic substance impregnated in the polymer. The dipping or spraying of the composition onto the stent can result in a complete coverage of all stent surfaces, i.e., both luminal (inner) and abluminal (outer) surfaces, with a coating. However, having a coating on the luminal surface of the stent can have a detrimental impact on the stent's deliverability as well as the coating's mechanical integrity. Moreover, from a therapeutic standpoint, the therapeutic agents on an inner surface of the stent get washed away by the blood flow and typically can provide for an insignificant therapeutic effect. In contrast, the agents on the outer surfaces of the stent are in contact with the lumen, and provide for the delivery of the agent directly to the tissues. Polymers of a stent coating also elicit a response from the body. Reducing the amount to foreign material can only be beneficial.

Briefly, an inflatable balloon of a catheter assembly is inserted into a hollow bore of a coated stent. The stent is securely mounted on the balloon by a crimping process. The balloon is inflated to implant the stent, deflated, and then withdrawn out from the bore of the stent. A polymeric coating on the inner surface of the stent can increase the coefficient of friction between the stent and the balloon of a catheter assembly on which the stent is crimped for delivery. Additionally, some polymers have a "sticky" or "tacky" consistency. If the polymeric material either increases the coefficient of friction or adherers to the catheter balloon, the effective release of the stent from the balloon after deflation can be compromised. If the stent coating adheres to the balloon, the coating, or parts thereof, can be pulled off the stent during the process of deflation and withdrawal of the balloon following the placement of the stent. Adhesive, polymeric stent coatings can also experience extensive balloon sheer damage post-deployment, which could result in a thrombogenic stent surface and possible embolic debris. The stent coating can stretch when the balloon is expanded and may delaminate as a result of such shear stress.

Accordingly, it is advantageous to eliminate the coating on the inner surface of the stent. Post crimping coating processes have been proposed for elimination of the coating on the inner surface of the stent. Briefly, subsequent to the mounting of the stent on the balloon, the stent can be dipped in the coating composition or the composition can be sprayed on the stent. Even though application of coating on the inner surface of the stent is eliminated, the coating is also deposited on the surface of the balloon between the stent struts. With this type of coating, the problems of adhesion of the stent to the balloon and formation of coating defects upon expansion, deflation and withdrawal of the balloon are not eliminated, and in effect, such problems could be further exasperated.

Coating of the stent prior to mounting of the stent on the balloon can also damage the coating on the outer surface of the stent. Stent crimping tools can cause coating defects on the stent by applying too much pressure at various directions to a soft polymeric coating. Harder or brittle polymers can have coating failure or crack under crimping pressure. Stent crimping is a critical step in manufacturing in that stent retention depends on it. Stent crimping is the act of affixing the stent to the delivery catheter or delivery balloon so that it remains affixed to the catheter or balloon until the physician desires to deliver the stent at the treatment site. Current stent crimping technology is sophisticated. A short time ago, one process used a roll crimper. This damaged many polymer coatings due to its inherent shearing action. Next came the collet crimper using metal jaws that are mounted into what is essentially a drill chuck. The jaws move in a purely radial direction. This movement was not expected to shear the coating, because it applied forces only normal to the stent surface. But some stent geometries require that stent struts scissor together during crimping. In those geometries, even if the crimper imposes only normal forces, the scissor action of the stent struts imparts shear. Finally, the iris or sliding-wedge crimper imparts mostly normal forces with some amount of tangential shear.

To use a roll crimper, first the stent is slid loosely onto the balloon portion of the catheter. This assembly is placed between the plates of the roll crimper. With an automated roll crimper, the plates come together and apply a specified amount of force. They then move back and forth a set distance in a direction that is perpendicular to the catheter. The catheter rolls back and forth under this motion, and the diameter of the stent is reduced. The process can be broken down into more than one step, each with its own level of force, translational distance, and number of cycles. With regard to a stent with a drug delivery coating, this process imparts a great deal of shear to the stent in a direction perpendicular to the catheter or catheter wall. Furthermore, as the stent is crimped, there is additional relative motion between the stent surface and the crimping plates. As a result, this crimping process tends to damage the stent coating.

The collet crimper is equally conceptually simple. A standard drill-chuck collet is equipped with several pie-piece-shaped jaws. These jaws move in a radial direction as an outer ring is turned. To use this crimper, a stent is loosely placed onto the balloon portion of a catheter and inserted in the center space between the jaws. Turning the outer ring causes the jaws to move inward. An issue with this device is determining or designing the crimping endpoint. One scheme is to engineer the jaws so that when they completely close, they touch and a center hole of a known diameter remains. Using this approach, turning the collet onto the collet stops crimps the stent to the known outer diameter. While this seems ideal, it can lead to problems. Stent struts have a tolerance on their thickness. Additionally, the process of folding non-compliant balloons is not exactly reproducible. Consequently, the collet crimper exerts a different amount of force on each stent in order to achieve the same final dimension. Unless this force, and the final crimped diameter, is carefully chosen, the variability of the stent and balloon dimensions can yield stent coating or balloon damage.

Furthermore, although the collet jaws move in a radial direction, they move closer together as they crimp. This action, combined with the scissoring motion of the struts, imparts tangential shear on the coatings that can also lead to damage. Lastly, the actual contact surfaces of the collet crimper are the jaw tips. These surfaces are quite small, and only form a cylindrical surface at the final point of crimping. Before that point, the load being applied to the stent surface is discontinuous.

In the sliding wedge or iris crimper, adjacent pie-piece-shaped sections move inward and twist, much like the leaves in a camera aperture. This crimper can be engineered to have two different types of endpoints. It can stop at a final diameter, or it can apply a fixed force and allow the final diameter to float. From the discussion on the collet crimper, there are advantages in applying a fixed level of force as variabilities in strut and balloon dimension will not change the crimping force. The sliding wedges impart primarily normal forces, which are the least damaging to stent coatings. As the wedges slide over each other, they impart some tangential force. But the shear damage is frequently equal to or less than that of the collet crimper. Lastly, the sliding wedge crimper presents a nearly cylindrical inner surface to the stent, even as it crimps. This means the crimping loads are distributed over the entire outer surface of the stent.

All current stent crimping methods were developed for all-metal stents. Stent metals, such as stainless steel, are durable and can take abuse. When crimping was too severe, it usually damaged the underlying balloon, not the stent. But polymeric coatings present different challenges.

The methods of the present invention provide for a solution by coating the outer surfaces of the stent post crimping or mounting of the stent to the balloon.

SUMMARY

A method of manufacturing a coated stent—balloon assembly is provided, comprising mounting a stent on a balloon of a catheter assembly; followed by forming a stent coating on the stent, wherein the section of the balloon surface over which the stent is mounted is free from any stent coating.

A method of manufacturing a coated stent—balloon assembly is provided, comprising forming a sacrificial layer on the balloon of a catheter assembly; followed by mounting a stent on a balloon, the stent including a struts separated by gaps; followed by forming a stent coating on the stent; followed by removal of the sacrificial layer.

A method of manufacturing a coated stent—balloon assembly is provided, comprising mounting a stent on a balloon, the stent including a struts separated by gaps; followed by forming a sacrificial layer on the balloon in the areas of the gaps between struts of the stent; followed by forming a coating on the stent; followed by removing the sacrificial layer, wherein the coating material remains on an outer surface of the stent.

BRIEF DESCRIPTION OF THE FIGURES

The figures have not been drawn to scale and, in particular, layers of FIGS. 3A-3E as well as 4A-4E have been over and under emphasized for illustrative purposes.

DETAILED DESCRIPTION

Figure 1:
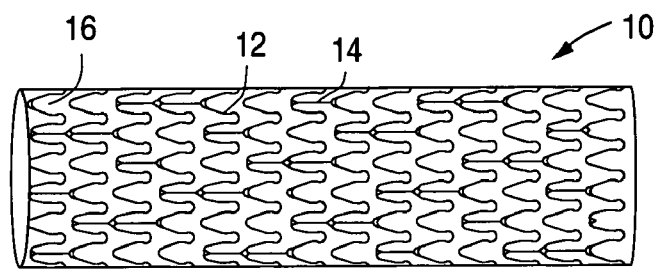
FIG. 1 illustrates a stent.

FIG. 1 illustrates a conventional stent 10. The embodiments of the invention should not be limited to the stent pattern illustrated in FIG. 1 as other types of stents can be coated by the methods described herein. Stent 10 is illustrated to have a scaffolding network which include struts 12 connected by elements 14 so as to have gaps 16 between struts 12. For ease of discussion, elements 14 can also be considered struts. Stents can be balloon expandable or self-expandable and can be used in a variety of medical applications and not just cardiovascular applications. The stent can be made from a metallic material, a polymeric material, such as those that are bioabsorabable, degradable, or erodable in kind, or a combination of both metallic material and polymers.

Figure 2:
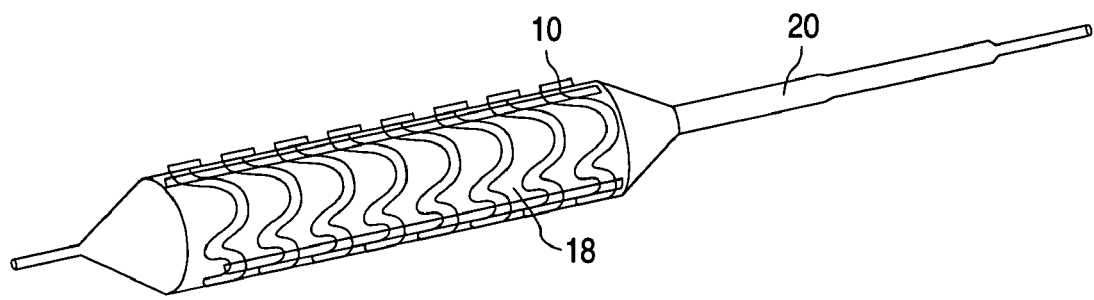
FIG. 2 illustrates a stent mounted on a balloon or expandable member of a catheter assembly.

FIG. 2 illustrates a stent 10 mounted on a balloon 18 of a catheter assembly 20. FIG. 2 illustrates a stent with a different pattern than the one in FIG. 1.

Figure 3A:
FIG. 3A-3E are steps for coating a stent mounted on a balloon in accordance with one embodiment of the invention.
Figure 3B:
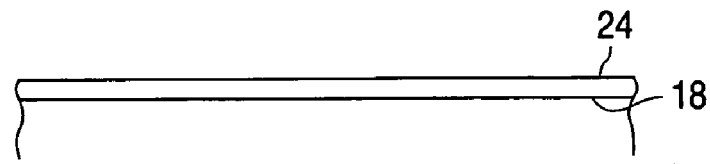
Figure 3C:
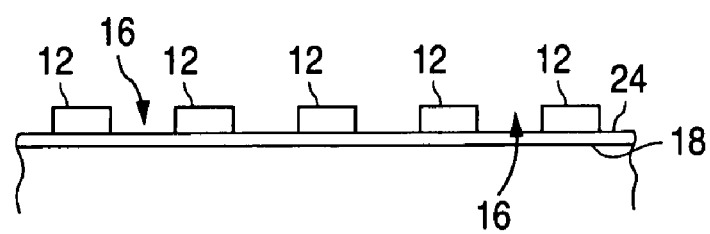
Figure 3D:
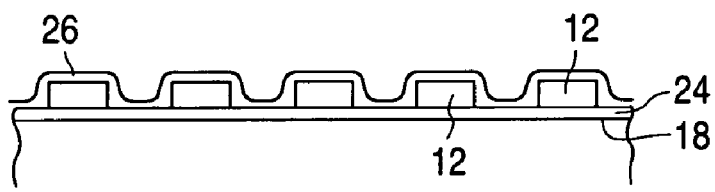
Figure 3E:
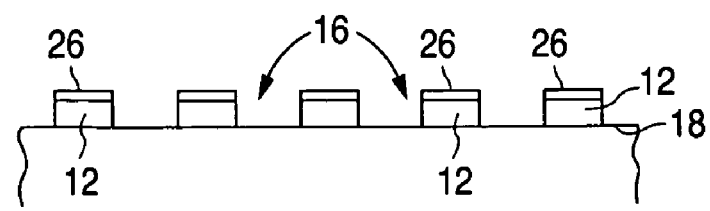

Referring to FIGS. 3A-3E, a method is illustrated for coating a stent in accordance with one embodiment of the invention. FIG. 3A is a partial cross section of balloon 18 having an outer face 22. On or over outer face 22 is deposited a sacrificial coating layer 24. The term "on" is intended to be used broadly, such that, for example a layer on a stent or a balloon is not intended to mean, unless otherwise specifically stated, surface contact between the layer and the stent or the layer and the balloon such that an intermediary layer or layers can be included. Subsequent to the deposition of the sacrificial coating layer 24, a stent, which in one embodiment, is free from any coating can be mounted or crimped on balloon 18 (for example, using SC700 MSI Stent Crimping Equipment, available from Machine Solutions, Inc., Flagstaff, Ariz.). FIG. 3C depicts struts 12 of the stent having gaps 16. A stent press can be used to further compress a stent to provide firmer engagement with balloon 18 (for example, using FFS700 MSI Balloon Form/Fold/Set Equipment, available from Machine Solutions, Inc.). In some embodiments, the stent can include a coating layer; however, this coating layer can be subject to damage during the crimping process. The damage can be cured by subsequent coating applications. FIG. 3D illustrates a stent coating 26 being uniformly applied over struts 12 and sacrificial layer 24. In some embodiments, a more selective coating process can be chosen to minimize application of the coating substance into gaps 16. Selective coating processes, such as those using an ink-jet type or micro-injector can limit the coating application to the outer surfaces of struts 12. Application of stent coating material is intended to include application of a single layer or multiple layers such that each layer can be the same or included different components and material. For example, some layers can be free of therapeutic substances or can be made from different polymeric materials. Prior to deposition of the stent coating material, a cleaning application, such as air-blasting, can be applied to the surface of struts 12 to clean off any residues or contaminants. In some embodiments, a wash can be employed as the cleaning application with the caveat that the wash does not remove sacrificial layer 24. The wash can be a non-solvent for sacrificial layer 24. Sacrificial layer 24 is removed, as illustrated in FIG. 3E causing the removal of coating 26 in gap regions 16. Surface 22 of balloon 18 can be free from any coating layer 26, at least in gaped regions 16 between struts 12. In some embodiments, crimping applies enough pressure to struts 12 so as to push the inner surface of struts 12 against outer surface 22 of balloon. As a result, sacrificial layer 24 is completely or substantially removed beneath struts 12. In some embodiments, sacrificial layer 24 can remain beneath struts 12 and eventually washed away in the body. This is applicable if sacrificial layer 24 is made from a bio-friendly material, such as materials that are non-toxic and non-inflammatory, and can be readily processed and eliminated by the body. In other embodiments, sacrificial layer 24 can be bioactive or include a bioactive material so as to provide therapeutic, prophylactic, and/or ameliorative effect for the patient. Once the stent is released, such agents can also be locally released into the system. In other embodiments, depending on the severity of the process of the removal of sacrificial layer 24, layer 24 under struts 12 can also be removed. Pressure can then be applied to the stent for firmer engagement with balloon 18.

Figure 4A:
FIG. 4A-4E are steps for coating a stent mounted on a balloon in accordance with one embodiment of the invention.
Figure 4B:
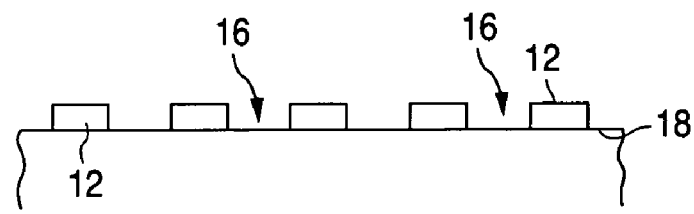
Figure 4C:
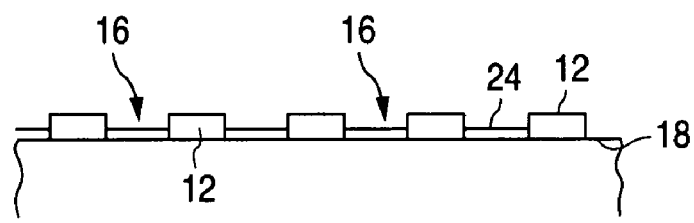
Figure 4D:
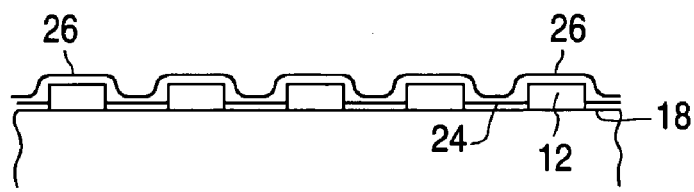
Figure 4E:
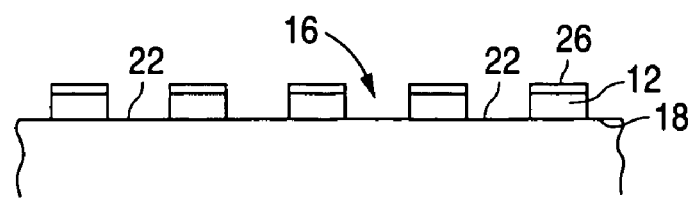

In accordance with another embodiment, referring to FIGS. 4A-4E, a stent is first mounted or crimped on balloon 18 and optionally further pressed as described above. The stent can optionally have a coating disposed thereon, but preferably is without a coating. FIG. 4B illustrates struts 12 on balloon 18. Sacrificial layer 24 is selectively deposited in gaps 16 on surface 22 of balloon 18 such that outer surface of struts 12 are not covered by layer 24. In some embodiments, deposition technique used could also cover struts 12 or there could be some incidental material deposited on struts 12. In such embodiments, an added step of removing sacrificial layer 24 over outer surface of struts 12 is required. This can be accomplished by, for example, application of a gas (e.g., forced air) or by scrapping. Stent coating 26 is then deposited on the stent-balloon assembly. Removal of sacrificial layer 24 facilitates removal of stent coating 26 in gaps 16 but not stent coating 26 on struts 12. Surface 22 of balloon 18 is free from stent coating material between struts 12 in gaped regions 16.

The application of the stent coating 26 should not allow for removal or dissolution of sacrificial layer 24. Some of sacrificial layer 24 may be incidentally removed but sufficient amount of layer 24 should be left behind so as to adequately remove the unwanted stent coating 26 portions. For example, if the coating material for the stent includes a solvent, this solvent should act as a non-solvent for sacrificial layer 24. Additionally, if a fluid is used to remove sacrificial layer 24, the fluid should be a non-solvent for the coating layer 26 so as not to remove or adversely affect the coating layer 26 of the stent.

To assist in the retention of sacrificial layer 24, an adhesive can be applied to surface of balloon or an adhesive can be combined with the sacrificial layer material. An adhesive can be especially useful if sacrificial layer 24 is deposited in a dry powder form as opposed to a solution or suspension. Representative examples of suitable adhesives include fibrin glue, cyanoacrylate, FOCALSEAL (polyethylene glycol based synthetic hydrogel), carboxymethyl cellulose, gelatin-resorcin-formaldehyde glue, silk elastin, tropoelastin added with an in situ cross-linker such as lysoyl peroxidase, and water soluble chitosan.

Sacrificial layer 24 can be made from or can include any substance that is capable of removing or disintegrating the coating material. Removal can be in bulk from. "Bulk form" refers to fragments of coating material as opposed to individual particles of coating material. Representative examples of material include oligosaccharides and polysaccharides such as sucrose (including caramel), dextrose, glucose and heparin; ionic salts such as sodium chloride, potassium chloride, copper sulfate, sodium bicarbonate and iodine salt; amino acids such as glycine; and polymers such as hyaluronic acid, poly(ethylene glycol) or polymers listed below. In one embodiment, the substance can be an active agent, drug or co-drug, including agents listed below. In some embodiments, the substance is made of a low molecular weight material, for example, a material that can be easily eliminated and discharged by the body or a material having a molecular weight less than 60 Daltons. In yet another embodiment, the substance includes ionic molecules.

In some embodiment of the present invention, sacrificial layer 24 can include or be made from a hydrophilic material. A substance is classified as "hydrophilic" or "hydrophobic" depending on the value of the substance's Hildebrand solubility parameter. The term "Hildebrand solubility parameter" is defined as a parameter 6 indicating the cohesive energy density of a substance. The δ parameter is determined as follows:

$$\delta = (\Delta E/V)^{1/2}$$

where δ is the solubility parameter, $(cal/cm^3)^{1/2}$; ΔE is the energy of vaporization, cal/mole; and V is the molar volume, $cm^3$/mole. "Hydrophilic" refers to a substance that has a Hildebrand solubility parameter equal to or greater than 8.5, 9, 9.5, 10, 10.5, 11, or alternatively 11.5 $(cal/cm^3)^{1/2}$.

In yet another embodiment, sacrificial layer 24 can be made from or include a material capable of absorbing a fluid. The substance can be a hydrogel. "Hydrogel" is intended to include a cross-linked polymer, via covalent, ionic, or hydrogen bonding, to form a three-dimensional open lattice structure which is capable of absorbing and entrapping water molecules to form a gel. Representative examples of hydrogels include poly(ethylene glycol), N-isopropylacrylamide, polyoxyethylene-polyoxypropylene block copolymers, poly(acrylic acid) grafted pluronic copolymers, chitosan grafted pluronic copolymer, elastin mimetic polypeptides, and combinations and mixtures thereof.

Sacrificial layer 24 and/or stent coating layer 26 can be deposited by spraying (e.g., EFD 780S spray device with VALVEMATE 7040 control system manufactured by EFD Inc., East Providence, R.I.), dipping, brushing, micro-injection, and the like. The deposition can be automated such as a micro-injection dispenser programmed to follow the pattern of the stent or to deposit sacrificial layer 24 in gaps 16 between stent struts 12 but not on outer surface of struts 12. An automated system is disclosed in U.S. Pat. No. 6,395,326. Masking techniques, as is known to one having ordinary skill in the art, can also be used for selective coating of a stent or balloon 18. Sacrificial layer 24 can be applied in dry powder form. Dry powder refers to a mass of particles that contains less than about 10%, less than 5%, less than 1%, less than 0.1%, or 0% residual fluid (e.g., solvent(s) or water). Alternatively, sacrificial layer 24 can be applied as a wet or semi-wet coating. For example, layer 24 material can be mixed with or dispersed in a liquid medium as particles, or can be partially or completely dissolved in a liquid carrier. If the material is combined with a liquid for deposition, the liquid can be allowed to evaporate before the application of the coating material. In some embodiments, however, it may be beneficial to apply the coating material to a wet or semi-wet sacrificial layer 24. This may allow sacrificial layer 24 to more effectively remove unwanted portions of coating layer 26. Wet and semi-wet coatings include 0.1%, 1%, 5%, or 10% or more water or solvent(s). Dry form can contain less than about 10%, less than 5%, less than 1%, less than 0.1%, or 0% residual fluid (e.g., solvent(s) or water). In some embodiments, it is preferred that the coating layer 26 be applied to a dry sacrificial layer 24.

In some embodiments, sacrificial layer 24 can be removed by application of a removal fluid. Application can be by dipping or spraying. As indicated above, this fluid should be a non-solvent for the stent coating. Representative examples of fluids that can be used to remove layer 24 include water;

alcohols including monohydric alcohols such as methanol, isopropyl alcohol and ethanol, dihydric alcohols and polyols; acetone; supercritical fluids such as supercritical carbon dioxide; and mixtures thereof. In one embodiment, the fluid is a mixture of supercritical carbon dioxide and one or more of methanol, isopropyl alcohol, ethanol and acetone. In another embodiment, the fluid is a mixture of water and an alcohol (e.g., 80/20% (w/w) water:alcohol). Preferably, the removal fluid is water or water-based. The fluid should be able dissolve sacrificial layer 24 or cause it to swell. In one embodiment, ultrasonic treatment or other vibrating type treatments can be employed to facilitate removal of layer 24. Post processing rinsing or application of an inert gas or air can be used to remove debris. It is believed that stent coating 26 which is in contact with sacrificial layer 26 will fail due to an interruption in the film structure by the swelling force or pressure. The selected duration of fluid exposure can depend on a variety of factors, such as the temperature, characteristics or type of the coating material, characteristics or type of the sacrificial layer, the potency of the removal fluid, the desired rate of removal, the cohesive and adhesion forces present on the coating, among other factors. For example, removal can be facilitated by deionized water at 37 deg. C. or at room temperature. The duration of the fluid exposure, for instance, can be from about 1 second to about 24 hours at ambient temperature.

Other means of removal are also included with the embodiments of the inventions. For example, laser application can be used to remove sacrificial layer 24 for removal of layer 26. Sacrificial layer 24 can be of the type that absorbs a great amount of energy and/or disintegrates readily so as to promote removal of coating layer 26.

In some embodiments, sacrificial layer 24 should have a relatively high coefficient of extinction, which allows the material to burn quickly and easily. The coefficient of extinction k is defined by:

$$k = \{Ln(I_0/I_f)\}/h$$

Where k=coefficient of extinction ($cm^{-1}$)
$I_0$=initial intensity
$I_f$=final intensity
h=distance at final intensity (cm)

A suitably high coefficient of extinction k can be greater than or equal to $1 \times 10^4$ $cm^{-1}$. Such materials may be particularly suitable for preventing melting defects when sacrificial layer 24 is removed using a laser.

Applying a coating material to a stent mounted on a balloon has significant advantages. As noted previously, in conventional coating techniques, stents are coated with a polymer before the stents are mounted on a delivery device. Because some of the polymers used in conventional techniques are brittle, these polymers are not able to withstand the pressure applied to the stents during mounting or crimping methods. The selective coating techniques of the present invention therefore allow a stent to be coated after the stent has been mounted on the delivery device thereby avoiding the need to subject the coating to the mounting and crimping processes. Therefore, one is able to select from a greater number of available polymers, even those that might prove to be too brittle for the convention processes.

The stent coating material can include one or a combination of a polymer (or polymers) or a therapeutic agent (or agents), with or without a fluid carrier or a solvent. Stent coating 26 can include layer(s) of pure polymer(s) or layer(s) of pure agent(s) or drug(s). Layer 26 can include multiple layers such a primer layer, a drug-reservoir layer, and a topcoat layer.

Examples of polymers that can be used include, but are not limited to, ethylene vinyl alcohol copolymer; polybutylmethacrylate; poly(ethylene-co-vinyl acetate); poly(vinylidene fluoride-co-hexafluororpropene); poly(hydroxyvalerate); poly(L-lactic acid); polycaprolactone; poly(lactide-co-glycolide); poly(hydroxybutyrate); poly(hydroxybutyrate-co-valerate); polydioxanone; polyorthoester; polyanhydride; poly(glycolic acid); poly(D, L-lactic acid); poly(glycolic acid-co-trimethylene carbonate); polyphosphoester; polyphosphoester urethane; poly (amino acids); cyanoacrylates; poly(trimethylene carbonate); poly(iminocarbonate); copoly(ether-esters) (e.g., PEO/PLA); polyalkylene oxalates; polyphosphazenes; biomolecules, such as fibrin, fibrinogen, cellulose, starch, collagen and hyaluronic acid; polyurethanes; silicones; polyesters; polyolefins; polyisobutylene and ethylene-alphaolefin copolymers; acrylic polymers and copolymers; vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile; polyvinyl ketones; polyvinyl aromatics, such as polystyrene; polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; polyamides, such as Nylon 66 and polycaprolactam; alkyd resins; polycarbonates; polyoxymethylenes; polyimides; polyethers; epoxy resins; polyurethanes; rayon; rayon-triacetate; cellulose acetate; cellulose butyrate; cellulose acetate butyrate; cellophane; cellulose nitrate; cellulose propionate; cellulose ethers; and carboxymethyl cellulose. KRATON G-1650 can also be used. KRATON is manufactured by Shell Chemicals Co. of Houston, Tex., and is a three block copolymer with hard polystyrene end blocks and a thermoplastic elastomeric poly(ethylene-butylene) soft middle block. KRATON G-1650 contains about 30 mass % of polystyrene blocks.

Therapeutic or bioactive agents can include any agent which is a therapeutic, prophylactic, diagnostic agent, and/or ameliorative. These agents can have anti-proliferative or anti-inflammmatory properties or can have other properties such as antineoplastic, antiplatelet, anti-coagulant, anti-fibrin, antithrombonic, antimitotic, antibiotic, antiallergic, antioxidant as well as cystostatic agents. Examples of suitable therapeutic and prophylactic agents include synthetic inorganic and organic compounds, proteins and peptides, polysaccharides and other sugars, lipids, and DNA and RNA nucleic acid sequences having therapeutic, prophylactic or diagnostic activities. Nucleic acid sequences include genes, antisense molecules which bind to complementary DNA to inhibit transcription, and ribozymes. Some other examples of other bioactive agents include antibodies, receptor ligands, enzymes, adhesion peptides, blood clotting factors, inhibitors or clot dissolving agents such as streptokinase and tissue plasminogen activator, antigens for immunization, hormones and growth factors, oligonucleotides such as antisense oligonucleotides and ribozymes and retroviral vectors for use in gene therapy. Examples of anti-proliferative agents include rapamycin and its functional or structural derivatives, 40-O-(2-hydroxy)ethyl-rapamycin (everolimus), and its functional or structural derivatives, paclitaxel and its functional and structural derivatives. Examples of rapamycin derivatives include methyl rapamycin (ABT-578), 40-O-(3-hydroxy)propyl-rapamycin, 40-O-[2-(2-hydroxy)ethoxy]ethyl-rapamycin, and 40-O-tetrazole-rapamycin. Examples of paclitaxel derivatives include docetaxel. Examples of antineoplastics and/or antimitotics include methotrexate, azathioprine, vincristine, vinblastine, fluorouracil, doxorubicin hydrochloride (e.g. ADRIAMYCIN from Pharmacia & Upjohn, Peapack N.J.), and mitomycin (e.g. MUTAMYCIN from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, thrombin inhibitors such as Angiema*-a ANGIOMAX A (Biogen, Inc., Cambridge, Mass.), calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name MEVACOR from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), nitric oxide or nitric oxide donors, super oxide dismutases, super oxide dismutase mimetic, 4-amino-2,2,6,6-tetramethylpiperidine-1-oxyl (4-amino-TEMPO), estradiol, anticancer agents, dietary supplements such as various vitamins, and a combination thereof. Examples of anti-inflammatory agents including steroidal and non-steroidal anti-inflammatory agents include tacrolimus, dexamethasone, clobetasol, combinations thereof. Examples of such cytostatic substance include angiopeptin, angiotensin converting enzyme inhibitors such as captopril (e.g. CAPOTEN and CAPOZIDE from Bristol-Myers Squibb Co., Stamford, Conn.), cilazapril or lisinopril (e.g.PRINIVIL and PRINZIDE from Merck & Co., Inc., Whitehouse Station, N.J.). An example of an antiallergic agent is permirolast potassium. Other therapeutic substances or agents which may be appropriate include alpha-interferon, bioactive RGD, and genetically engineered epithelial cells. The foregoing substances can also be used in the form of prodrugs or co-drugs thereof. The foregoing substances are listed by way of example and are not meant to be limiting. Other active agents which are currently available or that may be developed in the future are equally applicable.

Representative examples of solvents that can be combined with the polymer and/or active agent include chloroform, acetone, water (buffered saline), dimethylsulfoxide, propylene glycol methyl ether, iso-propylalcohol, n-propylalcohol, methanol, ethanol, tetrahydrofuran, dimethylformamide, dimethylacetamide, benzene, toluene, xylene, hexane, cyclohexane, pentane, heptane, octane, nonane, decane, decalin, ethyl acetate, butyl acetate, isobutyl acetate, isopropyl acetate, butanol, diacetone alcohol, benzyl alcohol, 2-butanone, cyclohexanone, dioxane, methylene chloride, carbon tetrachloride, tetrachloroethylene, tetrachloroethane, chlorobenzene, 1,1,1-trichloroethane, formamide, hexafluoroisopropanol, 1,1,1-trifluoroethanol, and hexamethyl phosphoramide, and a combination thereof.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A method of manufacturing a coated stent-balloon assembly, comprising:
    forming a sacrificial layer on a balloon of a catheter assembly prior to mounting a stent on the balloon;
    mounting the stent, having struts separated by gap regions, on the balloon; followed by
    forming a stent coating on the stent, comprising:
    depositing a coating material on the stent; and
    removing the sacrificial layer from the balloon, wherein the coating material remains on an outer surface of the stent, and areas of the balloon exposed by the gap regions of the stent are free from any stent coating.

2. The method of claim 1, wherein mounting of the stent on the balloon comprises crimping of the stent on the balloon so as to firmly engage the stent to the balloon.

3. The method of claim 1, wherein the sacrificial layer is removed by exposure of the balloon to a fluid.

4. The method of claim 1, wherein the sacrificial layer includes a material selected from a group of a polymer, an oligosaccharide, a polysaccharide, dextrose, glucose, heparin, an ionic salt, potassium chloride, copper sulfate, sodium bicarbonate, iodine salt, an amino acid, an active agent, a drug or a co-drug.

5. The method of claim 1, wherein the sacrificial layer includes a low molecular weight material.

6. The method of claim 1, wherein the sacrificial layer includes a material having a Hildebrand solubility parameter equal to or greater than $8.5$ $(cal/cm^3)^{1/2}$.

7. The method of claim 1, wherein the sacrificial layer includes a hydrogel.

8. The method of claim 7, wherein the hydrogel is selected from a group of poly(ethylene glycol), N-isopropylacrylamide, polyoxyethylene-polyoxypropylene block copolymer, poly(acrylic acid) grafted pluronic copolymer, chitosan grafted pluronic copolymer, elastin mimetic polypeptide, and combinations and mixtures thereof.

9. A method of manufacturing a coated stent-balloon assembly, comprising:
    mounting a stent, having struts separated by gap regions, on a balloon of a catheter assembly; followed by
    forming a stent coating on the stent, wherein areas of the balloon exposed by the gap regions of the stent are free from any stent coating, and forming the stent coating comprises:
    forming a sacrificial layer on the areas of the balloon exposed by the gap regions between the struts of the stent; followed by
    depositing a coating material on the stent; followed by
    removing the sacrificial layer, wherein the coating material remains on an outer surface of the stent.

10. The method of claim 9, wherein the sacrificial layer is removed by exposure of the balloon to a fluid.

11. The method of claim 9, wherein the sacrificial layer includes a material selected from a group of a polymer, an oligosaccharide, a polysaccharide, dextrose, glucose, heparin, an ionic salt, potassium chloride, copper sulfate, sodium bicarbonate, iodine salt, an amino acid, an active agent, a drug or a co-drug.

12. The method of claim 9, wherein the sacrificial layer includes a low molecular weight material.

13. The method of claim 9, wherein the sacrificial layer includes a material having a Hildebrand solubility parameter equal to or greater than $8.5$ $(cal/cm^3)^{1/2}$.

14. The method of claim 9, wherein the sacrificial layer includes a hydrogel.

15. The method of claim 14, wherein the hydrogel is selected from a group of poly(ethylene glycol), N-isopropylacrylamide, polyoxyethylene-polyoxypropylene block copolymer, poly(acrylic acid) grafted pluronic copolymer, chitosan grafted pluronic copolymer, elastin mimetic polypeptide, and combinations and mixtures thereof.

16. A method of manufacturing a coated stent-balloon assembly, comprising:

forming a sacrificial layer on a balloon of a catheter assembly; followed by mounting a stent on the balloon, the stent including struts separated by gaps; followed by forming a stent coating on the stent; followed by removal of all or substantially all of the sacrificial layer.

17. The method of claim 16, wherein some of the sacrificial layer beneath the struts of stent remains on the balloon subsequent to the removal of the sacrificial layer.

18. The method of claim 17, wherein the sacrificial layer includes an active agent or therapeutic substance.

19. A method of manufacturing a coated stent-balloon assembly, comprising:

mounting a stent on a balloon, the stent including struts separated by gaps; followed by forming a sacrificial layer on the balloon in the areas of the gaps between struts of the stent; followed by forming a coating on the stent; followed by removing the sacrificial layer, wherein the coating remains on an outer surface of the stent.

* * * * *

UNITED STATES PATENT AND TRADEMARK OFFICE
CERTIFICATE OF CORRECTION

PATENT NO. : 7,648,727 B2 Page 1 of 1
APPLICATION NO. : 10/928587
DATED : January 19, 2010
INVENTOR(S) : Hossainy et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1542 days.

Signed and Sealed this

Twenty-eighth Day of December, 2010

David J. Kappos
*Director of the United States Patent and Trademark Office*